United States Patent [19]

Jaeger et al.

[11] 4,248,222
[45] Feb. 3, 1981

[54] ENDOTRACHEAL TUBE HAVING A RELIEF VALVE

[75] Inventors: Friedrich Jaeger, Oberursel; Ludwig Lammers, Idstein, both of Fed. Rep. of Germany

[73] Assignee: Hoechst Aktiengesellschaft, Frankfurt am Main, Fed. Rep. of Germany

[21] Appl. No.: 5,803

[22] Filed: Jan. 23, 1979

[30] Foreign Application Priority Data

Jan. 25, 1978 [DE] Fed. Rep. of Germany ....... 2803094

[51] Int. Cl.³ ............................................ A61M 16/00
[52] U.S. Cl. ....................... 128/207.15; 128/349 BV; 137/860
[58] Field of Search ............... 128/348–351, 128/274, 207.15; 137/860

[56] References Cited

U.S. PATENT DOCUMENTS

| 3,129,784 | 4/1964 | Smallpeice | 137/860 X |
| 3,407,817 | 10/1968 | Galleher | 128/207.15 |
| 3,482,576 | 12/1969 | Ericson et al. | 128/349 BV |
| 3,504,822 | 4/1970 | Haloski | 137/860 X |
| 3,985,141 | 10/1976 | Stanley et al. | 128/351 |
| 4,000,741 | 1/1977 | Binard et al. | 128/349 BV X |
| 4,116,201 | 9/1978 | Shah | 128/351 |
| 4,147,170 | 4/1979 | Taylor | 128/351 |

FOREIGN PATENT DOCUMENTS

733890 7/1955 United Kingdom ............ 128/349 BV

*Primary Examiner*—Dalton L. Truluck
*Attorney, Agent, or Firm*—Curtis, Morris & Safford

[57] ABSTRACT

An endotracheal tube for single use, which is provided, at its end projecting into the windpipe, with an inflatable low-pressure sleeve and has an auxiliary tube which is suitable for inflating the low-pressure sleeve and carries a non-return valve and a relief valve, the relief valve consisting of a hollow body which has a lateral opening, and an elastic tubular skin, which covers the opening, being stretched around the hollow body.

11 Claims, 3 Drawing Figures

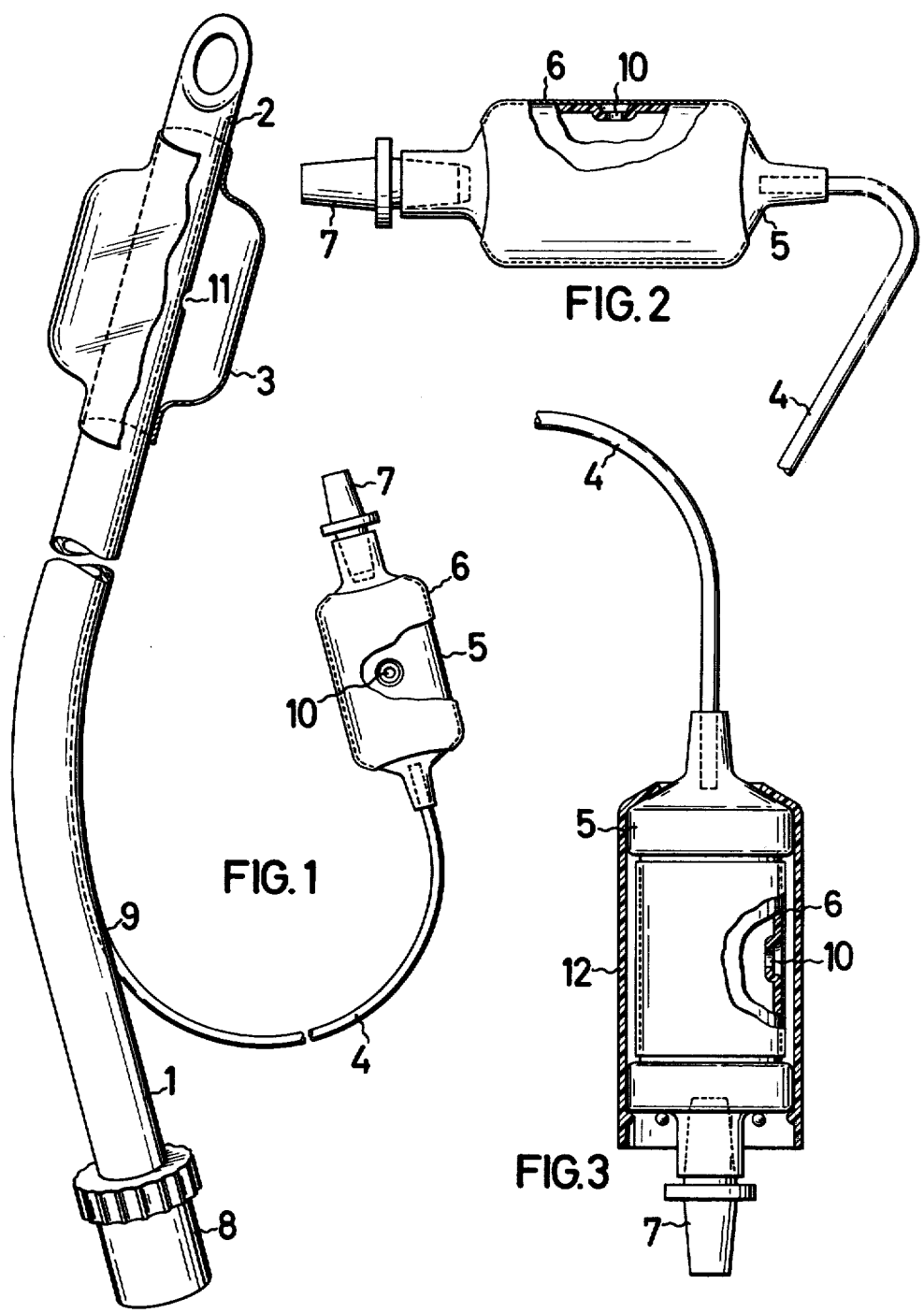

ENDOTRACHEAL TUBE HAVING A RELIEF VALVE

The invention relates to an endotracheal tube which has an inflatable low-pressure sleeve and in which the internal pressure is limited by means of a relief valve inserted into the inflation line.

In the case of certain diseases of the lung and the respiratory tract, it is necessary to supply the patient with air via an endotracheal tube. For this purpose, the endotracheal tube here has, at its distal end, an inflatable sleeve, by means of which the interspace between the inner wall of the windpipe and the outer wall of the respiration tube is sealed.

Earlier endotracheal tubes have a sleeve which is produced by drawing a piece of tubing of an elastic material over the tube and gluing it in at both ends. When such a sleeve is inflated, its surface is immediately extended and, as the size of the sleeve increases, a rising air pressure results in its interior. Until the sleeve lies against the tracheal wall of the patient, a certain internal pressure has been established, which is frequently considerably and can amount to several 100 mm Hg. Moreover, the contact pressure of the sleeve on the tracheal wall is not uniform since the sleeve, due to its inherent tension, tends to assume a circular cross-section, but the cross-sectional shape of the trachea is not round and the latter is thus forcibly pressed by the sleeve into an approximately round shape until a seal is made. It is not possible in this case to measure the contact pressure of the sleeve on the tracheal wall.

More recent endotracheal tubes use a low-pressure sleeve. This is a pre-formed sleeve which has the shape of a balloon and which, when the tube is introduced, lies in loose folds against the tube. In the following text, a low-pressure sleeve is understood as a sleeve, the circumference of which in the unstretched state is in general larger and in any case not smaller than the circumference of the trachea of the patient for whom it is intended. If a pre-formed low-pressure sleeve, the ends of which have a smaller diameter than its center, is glued at these two ends onto the tube, and is first evacuated and then slowly inflated, the sleeve, lying in folds, initially unfolds virtually without any excess pressure until all the slack has just been taken up. In this state, it has a defined circumference which may be called "circumference in the unstretched state". When such a tube is introduced, before inflation, into a glass tube having a diameter smaller than that of the unstretched low-pressure sleeve, it can be seen that on inflation virtually without any pressure, the center part of the sleeve makes contact in the glass tube, and folds which, depending on the dimensions, are more or less pronounced and extend substantially along the glass tube, are formed in the sleeve skin. If the pressure is increased in the sleeve, it is fully transmitted to the skin, which is not under tension in the part originally in contact, and from there it is transmitted in the same magnitude to the glass wall of the tube. If the air pressure is now measured, this gives at the same time the value of the pressure which is exerted by the sleeve skin on the wall of the glass tube. Transferring this procedure to the tracheal wall and the low-pressure sleeve, it can be seen that, in this case also, the inflation pressure of the sleeve is identical to the pressure exerted on the tracheal wall by the sleeve.

This relationship can now be exploited for applying endotracheal tubes with pressure-monitoring. Various technical devices have already been proposed, all of which have the aim of keeping the pressure so low, at 15 to 30 mm Hg, that the blood flow in the tracheal wall is not substantially impaired.

Thus, for example, it is already known to monitor the pressure in the sleeve by connecting the tubing for inflating the tube to a manometer and to supply, or to let off, the air for inflation in accordance with the indication on the manometer. Although the pressure by the sleeve on the tracheal wall can be controlled by the connection to a manometer, it is a disadvantage that an additional, frequently troublesome tubing is necessary for connecting the patient with the tube to the manometer and that measuring instruments of this type cause problems in maintaining sterile conditions, for example in the operating theater.

In German Offenlegungsschrift No. 2,353,153, an endotracheal tube has been disclosed in which the sleeve is intended partially to lift off radially from the respiration tube under a defined excess pressure of air and hence to act as a safety valve. However, it is very difficult technically to ensure that the desired valve action occurs reliably when the internal pressure of the sleeve exceeds a value of about 25 mm of mercury. It was therefore the object of the present invention to provide a cheap and simple relief valve, which nevertheless works reliably, for an endotracheal tube which avoids the disadvantages mentioned above.

The subject of the invention is an endotracheal tube for single use, which is provided, at its end projecting into the windpipe, with an inflatable low-pressure sleeve and has an auxiliary tube which is suitable for inflating the low-pressure sleeve and carries a non-return valve and a relief valve, wherein the relief valve consists of a hollow body having a lateral opening and an elastic tubular skin, covering the opening, is stretched around the hollow body. The said hollow body can preferably be cylindrical or spherically round. Appropriately, it is manufactured from a thermoplastic, rigid PVC having proved particularly suitable. The elastic tubular skin which covers the opening of the hollow body is preferably manufactured from natural rubber. The manufacture of the skin from natural rubber can be effected, for example, by the dipping process.

A preferred embodiment of the endotracheal tube having the relief valve is shown in FIGS. 1 to 3.

FIG. 1 represents an endotracheal tube constructed in accordance with this invention.

FIG. 2 depicts the hollow body, partially in cross-section, of the present invention illustrating the lateral opening in the hollow body.

FIG. 3 depicts another embodiment of the hollow body, partially in cross section, of the present invention illustrating a protective case for the hollow body.

The tube (1) has a large lumen for the passage of respiratory air and an auxiliary lumen, worked into the wall, for inflating the sleeve. The connector (8) for joining the tube to the respiration machine is fitted at the proximal end. The auxiliary lumen is sealed at the tip (2). The tip itself preferably has a finish which is x-ray opaque. The sleeve (3) is put on close to the distal end and it is connected to the auxiliary lumen by a notch (11) in the tube (1). At the point (9), the auxiliary lumen is likewise incised and the auxiliary tube (4) is inserted and glued in in such a way that it is connected to the auxiliary lumen in the direction of the distal end, while the auxiliary lumen at the point (9) is sealed in the direction of the proximal end.

The proximal end of the auxiliary tube (4) is connected to the hollow body (5), preferably by inserting and gluing it into the latter. In addition, it is also possible to interpose a test bag, not shown in the drawings, between the auxiliary tube and the hollow body, and the auxiliary tube can then be inserted into one side of the test bag and glued or welded and the other side of the test bag can be drawn over the nipple of the hollow body.

The hollow body (5) has a lateral opening (10) through which air can escape from the system. An elastic skin (6) is stretched around the hollow body (5), which skin seals the opening (10) and, under a defined air pressure in the sleeve and communicating with the latter, lifts off the hollow body and allows the air to escape. In this way, it acts as a relief valve. Since the pressure of the sleeve on the trachea is not to exceed the value of 25 mm Hg, the contact pressure of the elastic skin on the hollow body also must not be more than 25 mm Hg, and preferably the contact pressure should be 18 to 20 mm Hg. The hollow body is sealed by the non-return valve (7) which can, for example, be glued in. This valve (7) can be a normal non-return valve or it can be a valve which is mechanically pressed open by inserting the tip of a medical syringe and automatically closes when the syringe is withdrawn.

The elastic skin (6) can consist of a piece of tubing or it can be manufactured in a defined shape, for example as a dip molding of latex or another elastic material.

To ensure that, on the one hand, the elastic skin does not stick to the hollow body but, on the other hand, is nevertheless satisfactorily gas-tight, a thin film of silicone oil can be applied between the hollow body and the skin. To protect the elastic skin, it is also possible to draw a protective case (12) over the support body, for example as a tight push-fit.

Due to the logical design of the relief valve, the endotracheal tube, according to the invention, with a low-pressure sleeve prevents the pressure of the sleeve on the trachea from exceeding a value of 25 mm Hg, but at the same time it ensures a reliable seal of the interspace between the respiration tube and the trachea.

We claim:

1. An endotracheal tube comprising:
    a tubular member having a proximate and a distal end and a first lumen passing therethrough between said proximate and distal ends;
    an inflatable low pressure sleeve attached to said tubular member;
    an auxiliary tube member having a first open end, a second open end and a second lumen passing therethrough between the first and second open ends, said first open end communicating with said inflatable low pressure sleeve;
    a hollow body having continuous passage therethrough between a third open end and a fourth open end, said third open end communicating with said second open end of said auxiliary tube member;
    non-return valve means connected to said hollow body in said fourth open end for allowing inflation of the low pressure sleeve through said fourth open end, said hollow body and second lumen and for preventing deflation of said low pressure sleeve through said fourth open end; and
    relief valve means for allowing the deflation of said low pressure sleeve to a defined pressure when the pressure within said low pressure sleeve exceeds the defined pressure, said relief valve means including said hollow body being provided with an opening between said third and fourth open ends and an elastic tubular skin means, said skin means being substantially wider than said opening and being stretched around the outside of said hollow body for sealing said opening in the hollow body when the pressure within the pressure sleeve is below a defined pressure, for lifting away from the hollow body and allowing deflation of the low pressure sleeve to the defined pressure when said pressure in the low pressure sleeve exceeds the defined pressure and for providing resilient means for preventing deflation of the low pressure sleeve to a pressure below the defined pressure by resealing itself over the opening when the pressure in said low pressure sleeve is reduced to the defined pressure, whereby the pressure within said low pressure sleeve is maintained at the defined pressure.

2. The endotracheal tube, as claimed in claim 1, wherein the defined pressure is less than 25 mm Hg.

3. The endotracheal tube, as claimed in claim 1, wherein the defined pressure is 18 to 20 mm Hg.

4. The endotracheal tube, as claimed in claim 1 or 2, wherein the hollow body is spherical in shape.

5. The endotracheal tube, as claimed in claim 1 or 2, wherein the hollow body is cylindrical in shape.

6. The endotracheal tube, as claimed in claim 1 or 2, wherein the hollow body is a thermoplastic hollow body.

7. The endotracheal tube, as claimed in claim 6, wherein the hollow body is a rigid PVC hollow body.

8. The endotracheal tube, as claimed in claim 1 or 2, wherein the skin means includes a natural rubber skin means.

9. The endotracheal tube, as claimed in claim 1 or 2, wherein said relief valve means further includes a sealing and release agent between the hollow body and the elastic skin means.

10. The endotracheal tube, as claimed in claim 9, wherein said sealing and release agent is silicone oil.

11. The endotracheal tube, as claimed in claim 3, wherein said relief valve means further includes a sealing and release agent between the hollow body and said elastic skin means.

* * * * *